United States Patent [19]

Hattori et al.

[11] Patent Number: 4,567,427

[45] Date of Patent: Jan. 28, 1986

[54] METHOD NON-DESTRUCTIVELY IDENTIFYING DIFFERENT KINDS OF ROLLED STEEL FOR STRUCTURAL PURPOSES

[75] Inventors: Takeo Hattori, Yokohama; Tohru Sasakura, Tokyo, both of Japan

[73] Assignee: Samtec Company Limited, Tokyo, Japan

[21] Appl. No.: 567,321

[22] Filed: Dec. 30, 1983

[30] Foreign Application Priority Data

Apr. 25, 1983 [JP] Japan .................................. 58-71541

[51] Int. Cl.$^4$ ............................................ G01R 27/14
[52] U.S. Cl. ..................................................... 324/64
[58] Field of Search ................................ 324/64, 65 P

[56] References Cited

U.S. PATENT DOCUMENTS 2,094,234  9/1937  Drain, Jr. ................................ 324/64
3,308,418  2/1967  Rose ........................................ 324/64
3,611,125  10/1971 Press ....................................... 324/64
4,335,350  6/1982  Chen ....................................... 324/64

Primary Examiner—Stanley T. Krawczewicz
Attorney, Agent, or Firm—Holman & Stern

[57] ABSTRACT

A method of non-destructively identifying different kinds of rolled steel for structural purposes is disclosed, which is based on a synchronous detection process using a minute AC signal current. Four terminal probes arranged in a row and spaced apart at a precisely uniform pitch are held urged against a measuring surface of steel under test. The signal current is passed through the steel via the opposite end terminal probes. A potential difference is detected between the other two terminal probes. A resistivity corresponding to the detected potential difference is determined, and a corresponding value of silicon content in the steel is determined. The kind of steel is identified according to the determined silicon content.

6 Claims, 4 Drawing Figures

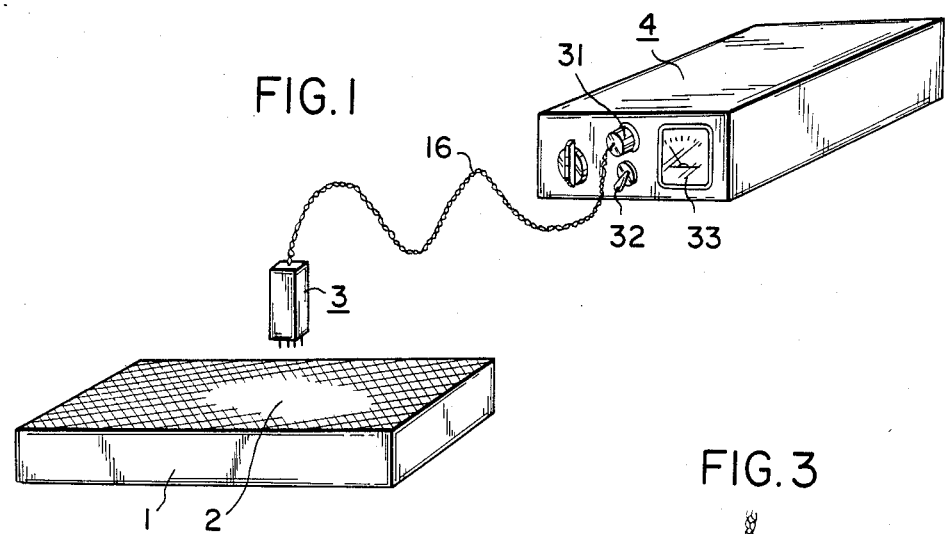
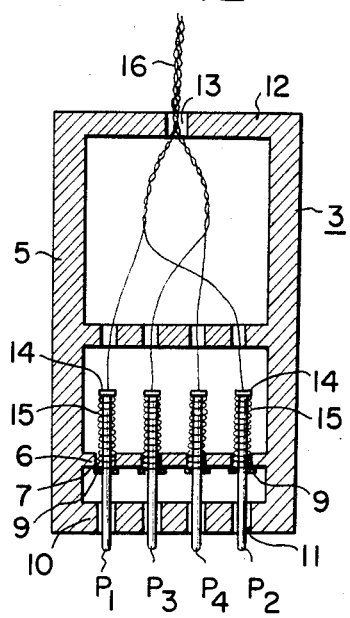
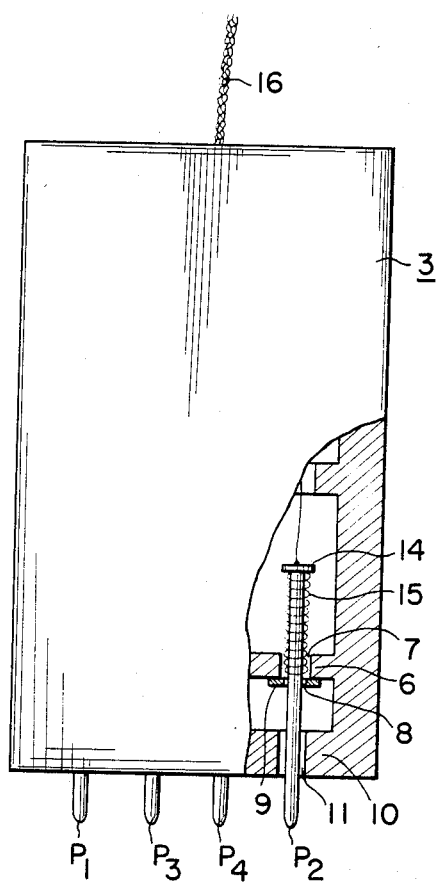

METHOD NON-DESTRUCTIVELY IDENTIFYING DIFFERENT KINDS OF ROLLED STEEL FOR STRUCTURAL PURPOSES

BACKGROUND OF THE INVENTION (a) Field of the Invention

This invention relates to a method of non-destructively identifying different kinds of rolled steel for structural purposes or like materials.

(b) Prior Art

Prior art methods of identifying different kinds of steel include one, in which mechanical properties of steel is determined from tensile tests and bending tests on test pieces, and one, in which chemical compositions of steel are determined by analytic tests on test samples. Usually, different kinds of steel are identified from certificates (mill sheets), on which the results of tests noted above are described, and also marks provided on steel. Therefore, it has been impossible to identify the kind of steel without any identification mark and after machining and assembly of steel.

Different kinds of steel cannot be identified by visual inspection. As a non-destructive method of identification, there is a spark test method. This method is standardized in Japan as spark test method for JIS G 0566 steel. To conduct this test, a light shield screen or partition member or a movable dark box is necessary for the purposes of preventing effects of wind and adjusting the brightness, under which the test is conducted. This method is effective for estimating different kinds of carbon steel for structural purposes containing carbon in a wide range from below 0.1% to above 0.6% and also stainless steel and other special alloy steel containing chromium, nickel, molybdenum, tungsten, etc. With this method, however, it is very difficult to identify different kinds of rolled steel for structural purposes. This is so because any structural rolled steel contains substantially an equal amount (i.e., 0.12 to 0.22%) of carbon. Especially, broadly used kinds of steel ASTM A 36 (which is referred to as SS41 in Japan) and ASTM A 573 (which is referred to as SM50 in Japan) are distinguished from each other in terms of the difference in the contents of silicon and manganese which can be hardly discriminated by the spark test.

SUMMARY OF THE INVENTION

An object of the invention is to provide a method of nondestructively identifying different kinds of rolled steel for structural purposes, particularly ASTM A 36 and ASTM A 573, by measuring the resistivity of steel.

According to the invention, there is provided a method of non-destructively identifying different kinds of rolled steel for strucural purposes, which comprises preparing an exposed measuring surface of steel under test, holding the tips of four resistivity measuring terminal probes in forced contact with the measuring surface in a straight line and at a uniform interval, passing a current at a low frequency between the opposite end terminal probes in the row, detecting the potential difference between the other two terminal probes than the opposite end terminal probes, determining a resistivity corresponding to the detected potential difference, determining a silicon content of the steel from the determined resistivity, and identifying the kind of steel according to the determined silicon content.

BRIEF DESCRIPTION OF THE DRAWINGS

In the drawings:

FIG. 1 is a perspective view showing a sensor and an amplifier constituting a steel resistivity measuring apparatus for carrying out an embodiment of the method according to the invention;

FIG. 2 is an enlarged-scale sectional view showing the sensor;

FIG. 3 is a partly broken-away enlarged-scale front view of the sensor; and

DETAILED DESCRIPTION OF THE INVENTION

Figure 4:
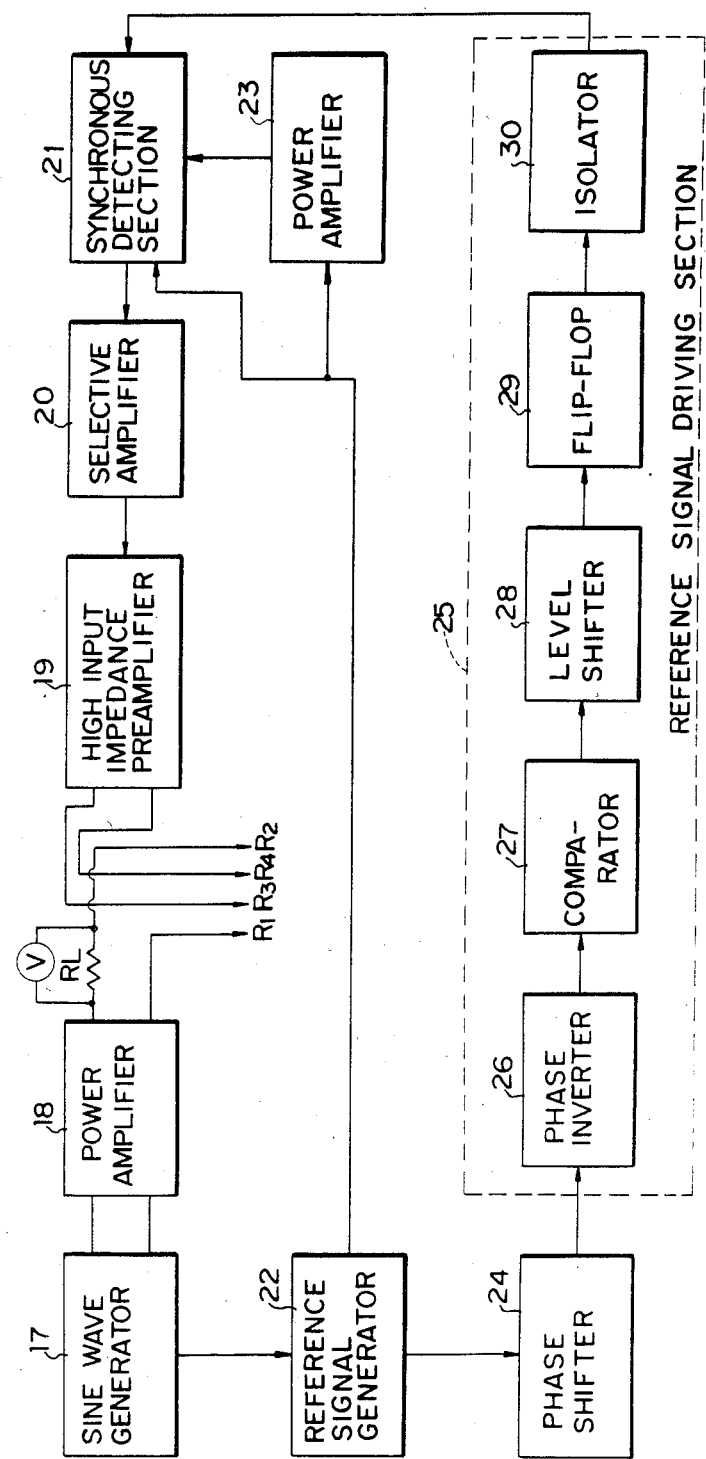
FIG. 4 is a block diagram showing the circuit construction of the amplifier.

Among various kinds of steel used steel structures, buildings, bridges, ships, tanks, towers, etc., the most extensively used kind is ASTM A 36, and the next most extensively used kind is ASTM A 573. These two kinds of steel are frequently used in combination to construct a structure, and it is very liable that the two kinds are mistaken for each other. Accordingly, it is important in practice to be able to identify these two kinds of steel. The two kinds of steel are entirely the same in appearance, color and weight although they are different in the tensile strength, welding properties, performance, cost and design conditions. Therefore, it has heretofore been impossible to distinguish them from each other, and this has posed serious problems in the industries concerned. It has been in practice by steel product dealers in Japan to mark edges of these two kinds of steel by white and yellow paints respectively to distinguish them from each other. However, this practice is subject to frequent errors. In the construction work for public office buildings, it is obligatory to check materials as to its identity. The checking is done by commonly termed destructive testing on test pieces cut away from the actual structure. Any of the checking methods, however, requires a great deal of experience, and materials, time and expenditures necessary for the inspection are very considerable. Nevertheless, no apparatus which can readily identify these two kinds of steel is available today.

Steel ASTM A 36 for general structures and steel ASTM A 573 for welded structures are featured by peculiar contents of silicon and manganese. The electric resistance of steel is increased with increasing content of silicon as is quantitatively evidenced by past metallurgical treatises.

The inventors have conducted extensive electrical measurements of the electric resistance of various commercially available kinds of steel for different manufacturers, different thicknesses and different sizes, and obtained a very quantitative relation between the silicon content and electric resistance.

Commercially available steel ASTM A 36 and ASTM A 573 are set apart in the silicon and manganese contents as follows.

|  | Si content (%) | Mn content (%) |
| --- | --- | --- |
| A 36 | 0.10 to 0.25 | 0.40 to 0.90 |
| A 573 | 0.25 to 0.45 | 1.20 to 1.50 |

The method according to the invention is predicated in the difference in the silicon content. More specifically, according to the invention the two kinds of steel are non-destructively identified by detecting the silicon content. It is well known in the art that the resistivity of steel is increased with increasing silicon content. Theoretically, therefore, the silicon content can be determined by measuring the resistivity. However, the resistivity is too low in value, typically of the order of several ten micro ohm-centimeters to be able to identify steel. Most of the conventional methods of measurement were based on the measurement of DC current and encountered various problems such as variations of the measurement with time (i.e, drift) and heat generation. Apparatuses which could solve these problems were very expensive and infeasible in practice. The invention is based on a practical and highly precise method of measurement of the resistivity. According to the invention, resort is had to a method of synchronous detection using a very minute AC signal.

An example of the invention will now be described with reference to the drawings. Before the measurement of the resistivity of steel 1, part of its surface oxide film (or commonly termed skin) is removed using a grinder or the like to prepare an exposed measuring surface 2. When the steel 1 is coated, the coating must also be removed.

The resistivity is measured by an apparatus, which comprises a sensor 3 and an amplifier 4 connected thereto. FIG. 2 shows the construction of the sensor 3. It comprises a casing 5 having an inner partition wall 6. The partition wall 6 has four small holes 7 formed at a uniform interval. Flange members 9 each having a small hole 8 of a smaller diameter than the holes 7 are secured to the lower side of the partition wall 6 such that each hole 8 is coaxial with each corresponding hole 7. A bottom wall 10 of the casing 5 has four small holes 11 formed right beneath the respective small holes 7 and 8 noted above. A top wall 12 of the casing 5 has a small hole 13. Needle-like probes $P_1$ to $P_4$ penetrate the respective small holes 7, 8 and 11, and their tip projects from the bottom 10 of the casing 5. Compression coil springs 15 are each fitted on each of the probes $P_1$ to $P_4$ between each flange mamber 9 secured to the lower surface of the partition wall 6 surrounding each small hole 7 and a flange 14 provided at the top of each probe. They urge the probes $P_1$ to $P_4$ against the measuring surface 2. The probes $P_1$ and $P_2$ are used as current terminals, while the probes $P_3$ and $P_4$ are used as voltage terminals. These probes $P_1$ to $P_4$ are connected by respective lead wires forming a cord 16 to the amplifier 4.

In this embodiment, the tips of the four probes $P_1$ to $P_4$ as respective terminals arranged in a row are spaced apart at a uniform internal of 1 mm with an allowance of ±5 microns. The allowance of the probe tip pitch has great influence on the measurement. If the error of the pitch exceeds 1/50 of the pitch, the error of the measurement would be too large to be able to identify the kind of steel. The probes $P_1$ to $P_4$ are urged by the compression coil springs 15 against the measuring surface 2, whereby an equal urging force is applied to them. With this arrangement, the tips of the probes $P_1$ to $P_4$ are reliably held in contact with the measuring surface 2 and the contact resistance will not vary greatly even if the measuring surface 2 is somewhat rougth. The compression coil springs 15 for controlling the urging force applied to the probes $P_1$ to $P_4$ may be replaced with leaf springs or other elastic members such as hard rubber members. The probes $P_1$ to $P_4$ are made of a material of high hardness to avoid changes in the contact resistance in long use. They have a tapering tip portion and a spherical tip of a constant diameter.

FIG. 4 shows the circuit construction of the amplifier 4. Referring to the Figure, a sine wave generator 17 generates a sine wave at a low frequency. It includes a wing bridge type oscillator consisting of an operational amplifier and an amplitude limiting diode. A power amplifier 18 supplies current to the steel 1 under test to build up a potential difference necessary for the measurement. The measurement current is passed to flow through the steel 1 through the current terminals $P_1$ and $P_2$ and a resistor RL. The current passed through the steel 1 is monitored using an electronic AC voltmeter V connected across the resistor RL. The current can be varied by a variable resistor provided in the sine wave generator 17. The sensor 3 noted above is constituted by the voltage terminals $P_3$ and $P_4$, the tips of which are found on the line connecting the tips of the opposite end current terminals $P_1$ and $P_2$ and are also in contact with the measuring surface 2 of the steel 1 under test. The postential difference between the terminals $P_3$ and $P_4$ is detected. A high input impedance preamplifier 19 is connected to the voltage terminals $P_3$ and $P_4$. A selective amplifier 20 selectively amplifies only a signal frequency component of the output of the preamplifier 19, thereby improving the signal-to-noise ratio. A synchronous detecting section 21 includes an in-phase analog switch, an opposite phase analog switch and an amplifier for amplifying the switch outputs. The analog switches are on-off operated by a reference signal from a reference signal generator 22 synchronized to the signal frequency. A power amplifier 23 effects necessary power amplification to the synchronous detection output to provide power for driving an external apparatus such as a meter. A phase shifter 24 includes a ramp wave generating circuit synchronized to the signal and a PLL circuit. A desired phase component of the signal voltage generated across the measuring surface 2 of the steel 1 can be detected by appropriately adjusting the phase of the phase shifter 24. The phase of the phase shifter is adjusted to obtain a DC output corresponding to the resistance and reactance of the measuring surface 2. A reference signal driving section 25 includes a phase inverter 26, a comparator 27, a level shifter 28, a flip-flop 29 and an isolator 30. The phase inverter 26 inverts the ramp wave fed from the phase shifter 24, and an in-phase and opposite phase ramp waves are fed to the comparator 27, which consists of two operational amplifiers. The comparator 27 feeds pulse waves 180 degrees out of phase from each other to the level shifter 28, which consists of two transistors. The flip-flop 29 is driven by the output of the level shifter 28 to produce an exact rectangular wave synchronized to the oscillation frequency of the sine wave generator 17. The ground potential of the sine wave generator 17 and the ground potential of the sensor 3 are different. Accordingly, the synchronous detecting section 21 is isolated by a photo-coupler.

To measure the resistivity of the steel 1 with the measuring apparatus having the construction described above, a plug 31 of the cord 16 of the sensor 3 is connected to a connector plug receptacle of the amplifier 4, a power switch 32 is turned on, and the tips of the terminal probes $P_1$ to $P_4$ are held in forced contact with the measuring surface 2. A current is thus caused to flow through the steel 1 via the current terminals $P_1$ and $P_2$. This current has a level corresponding to a potential difference necessary for the detection, and it is provided from the power amplifier 18 as a result of power amplification of a minute signal current at a low frequency from the sine wave generator 17. In this embodiment, the low frequency of the signal current is set to 20 Hz. The frequency is desirably in a range between 10 and 60 Hz. It is found that if the frequency exceeds 1 kHz, the error of the measurement is too large so that the identification of the kind of steel is difficult.

The current flows through the steel 1 along the terminals $P_1$, $P_3$, $P_4$ and $P_2$. The potential difference detected between the voltage terminals $P_3$ and $P_4$ is related to the resistivity of the steel 1; it is high when the resistivity is high and small with a low resistivity. The detected potential difference is displayed on a display meter 33. The silicon content is indirectly known from a value of the quantitatively obtained electric resistance noted before corresponding to the measured resistivity of the steel 1. In this way, it is determined that the steel 1 under test is ASTM A 36 or ASTM A 573.

In the operation described above, the signal-to-noise ratio is improved in that only the signal frequency component is selectively amplified by the selective amplifier 20 in the amplifier 4.

When the measurement current is other than the level corresponding to the potential difference necessary for detection, it is adjusted to the necessary level by the variable resistor. The current value is monitored by the electronic AC voltmeter V connected across the resistor RL.

As has been described in the foregoing, the identification of the kind of steel for structural purposes, which has been difficult with the prior art spark test method, can be done even by one who is unskilled. Further, the method according to the invention permits non-destructive indentification of the kind of structural rolled steel in outdoor material stocks, construction cites or in existing building structures easily and without need of any skill. Thus, it is possible to find or prevent use of steel other than specified and identify unknown kind of steel. Otherwise possible hazard thus can be eliminated, as well as saving a great deal of labor that has heretofore been necessary for identification.

The method according to the invention can also be utilized for the identification of a variety of different kinds of steel other than the structural rolled steel. Furthermore, it is applicable for apparatus for identifying materials other than steel, apparatus for measuring very slight electric resistance, flaw detector, etc.

What is claimed is:

1. A method of non-destructively identifying different kinds of rolled steel for structural purposes comprising the steps of:

removing the coating film and/or oxide film of part of the surface of structural rolled steel under test to provide an exposed measuring surface;

holding the tips of four resistivity measuring terminal probes in forced contact with said measuring surface in along a straight line and at a uniform interval;

passing a current at a low frequency between the opposite end terminal probes in the row;

detecting the potential difference between the other two terminal probes than the opposite end terminal probes;

determining a resistivity corresponding to said detected potential difference;

determining a silicon content of the steel under test according to said determined resistivity;

and identifying the kind of the steel under test from said determined silicon content.

2. The method according to claim 1, wherein the allowance of the pitch of arrangement of the tips of said terminal probes is within 1/50 of said pitch.

3. The method according to claim 1, wherein the frequency of said current passed between said opposite end terminal probes is not higher than 1 kHz.

4. The method according to claim 1, wherein said detected potential difference between said opposite end terminal probes is coupled to a selective amplifier for selectively amplifying only the signal frequency component.

5. The method according to claim 4, wherein the output of said eleective amplifier is converted into a corresponding resistivity.

6. The method according to claim 5, wherein said resistivity is displayed.

* * * * *